United States Patent
Canovas Vidal et al.

(10) Patent No.: US 9,817,246 B2
(45) Date of Patent: Nov. 14, 2017

(54) MULTIFOCAL LENS HAVING AN OPTICAL ADD POWER PROGRESSION, AND A SYSTEM AND METHOD OF PROVIDING SAME

(75) Inventors: Carmen Canovas Vidal, Groningen (NL); Marrie H. Van Der Mooren, Engelbert (NL); Hendrik A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 485 days.

(21) Appl. No.: 13/309,314

(22) Filed: Dec. 1, 2011

(65) Prior Publication Data
US 2012/0143326 A1 Jun. 7, 2012

Related U.S. Application Data

(60) Provisional application No. 61/418,759, filed on Dec. 1, 2010.

(51) Int. Cl.
*A61F 2/16* (2006.01)
*G02C 7/04* (2006.01)

(52) U.S. Cl.
CPC ............ *G02C 7/045* (2013.01); *A61F 2/1616* (2013.01); *G02C 7/042* (2013.01)

(58) Field of Classification Search
CPC .................................................. A61F 2/1616
USPC ................ 623/6.23, 6.24, 627–629
See application file for complete search history.

(56) References Cited

U.S. PATENT DOCUMENTS

| | | | |
|---|---|---|---|
| 5,766,244 A * | 6/1998 | Binder ........................ | 623/6.54 |
| 6,086,203 A * | 7/2000 | Blum et al. .............. | 351/159.42 |
| 6,409,339 B1 | 6/2002 | Wanders | |
| 6,540,353 B1 * | 4/2003 | Dunn ....................... | 351/159.47 |
| 2004/0207807 A1 | 10/2004 | Lindacher | |
| 2009/0323020 A1 | 12/2009 | Zhao et al. | |
| 2010/0066973 A1 | 3/2010 | Portney | |

(Continued)

FOREIGN PATENT DOCUMENTS

| | | |
|---|---|---|
| WO | WO2004068214 A1 | 8/2004 |
| WO | WO2009017403 A1 | 2/2009 |

OTHER PUBLICATIONS

International Search Report and Written Opinion for Application No. PCT/IB2011/003000, dated Apr. 3, 2012, 13 pages.

(Continued)

*Primary Examiner* — Corrine McDermott
*Assistant Examiner* — Joshua Levine
(74) *Attorney, Agent, or Firm* — Abbott Medical Optics Inc.

(57) ABSTRACT

An apparatus, system and method including an ophthalmic lens having an optic with an anterior surface, a posterior surface, and an optical axis. The ophthalmic lens further includes a first region having a first optical power and a second region having a second optical power. The ophthalmic lens further includes a third region having an optical power that progresses from the first optical power to the second optical power. The progression may be uniform or non-uniform. Each of the first, second and progression optical power may include a base power and an optical add power. Each of the first, second and progression regions may provide a first focus, a second focus and a plurality of third foci, respectively.

14 Claims, 19 Drawing Sheets

(56) References Cited

U.S. PATENT DOCUMENTS

2010/0097569 A1    4/2010  Weeber et al.
2010/0315589 A1*  12/2010  Portney .................... 351/160 R
2012/0143326 A1*   6/2012  Canovas Vidal ..... A61F 2/1616
                                                    623/6.27

OTHER PUBLICATIONS

Wolffsohn J.S., et al., "Visual Function in Patient's Implanted with a Non-Concentric Multifocal Intraocular Lens," 2010.

\* cited by examiner

Figure 9(N)

| | | |
|---|---|---|
| | ..... | . |
| Z 2 | 0.000 | 4^(1/2) (p) * COS (A) |
| Z 3 | 0.754 | 4^(1/2) (p) * SIN (A) |
| Z 4 | 1.097 | 3^(1/2) (2p^2 - 1) |
| Z 5 | 0.000 | 6^(1/2) (p^2) * SIN (2A) |
| Z 6 | -0.605 | 6^(1/2) (p^2) * COS (2A) |
| Z 7 | 0.244 | 8^(1/2) (3p^3 - 2p) * SIN (A) |
| Z 8 | 0.000 | 8^(1/2) (3p^3 - 2p) * COS (A) |
| Z 9 | -0.244 | 8^(1/2) (p^3) * SIN (3A) |
| Z 10 | 0.000 | 8^(1/2) (p^3) * COS (3A) |
| Z 11 | 0.218 | 5^(1/2) (6p^4 - 6p^2 + 1) |
| Z 12 | -0.080 | 10^(1/2) (4p^4 - 3p^2) * COS (2A) |
| Z 13 | 0.000 | 10^(1/2) (4p^4 - 3p^2) * SIN (2A) |
| Z 14 | 0.080 | 10^(1/2) (p^4) * COS (4A) |
| Z 15 | 0.000 | 10^(1/2) (p^4) * SIN (4A) |
| Z 16 | 0.000 | 12^(1/2) (10p^5 - 12p^3 + 3p) * COS (A) |
| Z 17 | -0.012 | 12^(1/2) (10p^5 - 12p^3 + 3p) * SIN (A) |
| Z 18 | 0.000 | 12^(1/2) (5p^5 - 4p^3) * COS (3A) |
| Z 19 | 0.012 | 12^(1/2) (5p^5 - 4p^3) * SIN (3A) |
| Z 20 | 0.000 | 12^(1/2) (p^5) * COS (5A) |
| Z 21 | -0.012 | 12^(1/2) (p^5) * SIN (5A) |
| Z 22 | -0.017 | 7^(1/2) (20p^6 - 30p^4 + 12p^2 - 1) |
| Z 23 | 0.000 | 14^(1/2) (15p^6 - 20p^4 + 6p^2) * SIN (2A) |
| Z 24 | 0.027 | 14^(1/2) (15p^6 - 20p^4 + 6p^2) * COS (2A) |
| Z 25 | 0.000 | 14^(1/2) (6p^6 - 5p^4) * SIN (4A) |
| Z 26 | -0.027 | 14^(1/2) (6p^6 - 5p^4) * COS (4A) |
| Z 27 | 0.000 | 14^(1/2) (p^6) * SIN (6A) |
| Z 28 | 0.027 | 14^(1/2) (p^6) * COS (6A) |

Figure 12(N)

| | | |
|---|---|---|
| Z 1 | 1.123 | : 1 |
| Z 2 | 0.000 | : 4^(1/2) (p) * COS (A) |
| Z 3 | 0.734 | : 4^(1/2) (p) * SIN (A) |
| Z 4 | 0.874 | : 3^(1/2) (2p^2 - 1) |
| Z 5 | 0.000 | : 6^(1/2) (p^2) * SIN (2A) |
| Z 6 | -0.112 | : 6^(1/2) (p^2) * COS (2A) |
| Z 7 | 0.240 | : 8^(1/2) (3p^3 - 2p) * SIN (A) |
| Z 8 | 0.000 | : 8^(1/2) (3p^3 - 2p) * COS (A) |
| Z 9 | -0.241 | : 8^(1/2) (p^3) * SIN (3A) |
| Z 10 | 0.000 | : 8^(1/2) (p^3) * COS (3A) |
| Z 11 | 0.176 | : 5^(1/2) (6p^4 - 6p^2 + 1) |
| Z 12 | -0.024 | : 10^(1/2) (4p^4 - 3p^2) * COS (2A) |
| Z 13 | 0.000 | : 10^(1/2) (4p^4 - 3p^2) * SIN (2A) |
| Z 14 | 0.025 | : 10^(1/2) (p^4) * COS (4A) |
| Z 15 | 0.000 | : 10^(1/2) (p^4) * SIN (4A) |
| Z 16 | 0.000 | : 12^(1/2) (10p^5 - 12p^3 + 3p) * COS (A) |
| Z 17 | -0.010 | : 12^(1/2) (10p^5 - 12p^3 + 3p) * SIN (A) |
| Z 18 | 0.000 | : 12^(1/2) (5p^5 - 4p^3) * COS (3A) |
| Z 19 | 0.010 | : 12^(1/2) (5p^5 - 4p^3) * SIN (3A) |
| Z 20 | 0.000 | : 12^(1/2) (p^5) * COS (5A) |
| Z 21 | -0.010 | : 12^(1/2) (p^5) * SIN (5A) |
| Z 22 | 0.001 | : 7^(1/2) (20p^6 - 30p^4 + 12p^2 - 1) |
| Z 23 | 0.000 | : 14^(1/2) (15p^6 - 20p^4 + 6p^2) * SIN (2A) |
| Z 24 | 0.002 | : 14^(1/2) (15p^6 - 20p^4 + 6p^2) * COS (2A) |
| Z 25 | 0.000 | : 14^(1/2) (6p^6 - 5p^4) * SIN (4A) |
| Z 26 | -0.002 | : 14^(1/2) (6p^6 - 5p^4) * COS (4A) |
| Z 27 | 0.000 | : 14^(1/2) (p^6) * SIN (6A) |
| Z 28 | 0.002 | : 14^(1/2) (p^6) * COS (6A) |

Figure 15(N)

| | | |
|---|---|---|
| Z 1 | 1.945 | : 1 |
| Z 2 | 0.754 | : $4^{(1/2)} (p) * \cos(A)$ |
| Z 3 | 0.735 | : $4^{(1/2)} (p) * \sin(A)$ |
| Z 4 | 1.457 | : $3^{(1/2)} (2p^2 - 1)$ |
| Z 5 | 0.000 | : $6^{(1/2)} (p^2) * \sin(2A)$ |
| Z 6 | 0.022 | : $6^{(1/2)} (p^2) * \cos(2A)$ |
| Z 7 | 0.241 | : $8^{(1/2)} (3p^3 - 2p) * \sin(A)$ |
| Z 8 | 0.243 | : $8^{(1/2)} (3p^3 - 2p) * \cos(A)$ |
| Z 9 | -0.241 | : $8^{(1/2)} (p^3) * \sin(3A)$ |
| Z 10 | 0.244 | : $8^{(1/2)} (p^3) * \cos(3A)$ |
| Z 11 | 0.234 | : $5^{(1/2)} (6p^4 - 6p^2 + 1)$ |
| Z 12 | 0.056 | : $10^{(1/2)} (4p^4 - 3p^2) * \cos(2A)$ |
| Z 13 | 0.000 | : $10^{(1/2)} (4p^4 - 3p^2) * \sin(2A)$ |
| Z 14 | 0.105 | : $10^{(1/2)} (p^4) * \cos(4A)$ |
| Z 15 | 0.000 | : $10^{(1/2)} (p^4) * \sin(4A)$ |
| Z 16 | -0.012 | : $12^{(1/2)} (10p^5 - 12p^3 + 3p) * \cos(A)$ |
| Z 17 | -0.011 | : $12^{(1/2)} (10p^5 - 12p^3 + 3p) * \sin(A)$ |
| Z 18 | -0.012 | : $12^{(1/2)} (5p^5 - 4p^3) * \cos(3A)$ |
| Z 19 | 0.010 | : $12^{(1/2)} (5p^5 - 4p^3) * \sin(3A)$ |
| Z 20 | -0.012 | : $12^{(1/2)} (p^5) * \cos(5A)$ |
| Z 21 | -0.010 | : $12^{(1/2)} (p^5) * \sin(5A)$ |
| Z 22 | -0.019 | : $7^{(1/2)} (20p^6 - 30p^4 + 12p^2 - 1)$ |
| Z 23 | 0.000 | : $14^{(1/2)} (15p^6 - 20p^4 + 6p^2) * \sin(2A)$ |
| Z 24 | -0.025 | : $14^{(1/2)} (15p^6 - 20p^4 + 6p^2) * \cos(2A)$ |
| Z 25 | 0.000 | : $14^{(1/2)} (6p^6 - 5p^4) * \sin(4A)$ |
| Z 26 | -0.029 | : $14^{(1/2)} (6p^6 - 5p^4) * \cos(4A)$ |
| Z 27 | 0.000 | : $14^{(1/2)} (p^6) * \sin(6A)$ |
| Z 28 | -0.025 | : $14^{(1/2)} (p^6) * \cos(6A)$ |

Figure 17

| Pupil diameter (mm) | Far distance area (%) | Power progression area (%) | Near focus area (%) | Increasing ratio far/near related to 3mm |
|---|---|---|---|---|
| 3 | 20 | 80 | 0 | |
| 4 | 26.71 | 66 | 7.2 | 6.7/7.2 = 0.93 |
| 5 | 31.1 | 54.5 | 14.4 | 11.1/14.4 = 0.76 |
| 6 | 34.3 | 46.1 | 19.6 | 14.2/19.6 = 0.72 |

# MULTIFOCAL LENS HAVING AN OPTICAL ADD POWER PROGRESSION, AND A SYSTEM AND METHOD OF PROVIDING SAME

CROSS-REFERENCE TO RELATED PATENTS AND APPLICATIONS

The present application claims priority under 35 U.S.C §119(e) to provisional application No. 61/418,759, filed on Dec. 1, 2010, which is incorporated herein by reference in its entirety. Full Paris Convention priority is hereby expressly reserved.

BACKGROUND OF THE INVENTION

Field of the Invention

This invention relates generally to ophthalmic lenses, and more specifically to a multifocal ophthalmic lens having an optical add power progression, as well as a system and method for providing such a multifocal ophthalmic lens.

Description of the Background

An ophthalmic lens, such as an intraocular lens (IOL), a phakic IOL, or a corneal implant, by way of non-limiting example, may be used to enhance patient vision. For example, an IOL may be used to replace the natural lens of an eye that is removed during cataract surgery.

Multifocal lenses, including multifocal IOLs, may replace the function of the eye's natural lens in providing multifocal vision, such as by dividing incident light to two different focal points to provide both near and distance vision. The use of diffractive or refractive optics in ophthalmic lenses, in order to provide multifocal/bifocal division of incident light, is well understood to those skilled in the pertinent arts.

In a bifocal IOL, the optic area may be divided into a plurality of annular zones that are offset parallel to the optical axis to provide a specific diffractive or refractive relationship between the zones. As used herein, "annular" is defined to be ring-shaped, substantially ring-shaped, or at least partially ring-shaped. The annular zones may form a concentrically arranged pattern characterized by the optical power step between zones, the circumferential spacing between zones, and the surface profile of each zone. These concentric annular zones are typically configured to maintain a predefined relationship of light passing through the zones to effect bifocal vision. Unfortunately, the abrupt optical power step between zones makes it difficult for such a solution to provide improved far and near vision simultaneously, while avoiding glare, halos, decreased contrast sensitivity, and increased pupil dependence. Further, such solutions are not designed to achieve intermediate vision, which would optimally correct presbyopia.

In known alternative embodiments of a multifocal lens, the zones may be non-radially symmetric (see the Lentis MPlus® lens by OcuLentis), such as in the embodiment illustrated in FIG. 1 as 23b. More particularly, center and upper zones may be at least substantially circular and semi-circular respectively, and may have thereabout below a portion having a different optical power than the center and upper zone. In such a lens, the upper and central portion of the optic may be used for distance vision, and the optical add power may be constrained to the lower portion of the lens, in the non-radially symmetric distribution, as would be the case for a bifocal spectacle lens. As used herein, the term "non-radially symmetric" is used to indicate that the distribution is not the same for all the points at the same distance from the center of the optic in the lens plane.

As such, the zones of these exemplary bifocal IOLs may form a bifocal lens that may, for example, produce a first focal point for distant vision, and a second focal point corresponding to near distances. A preferred characteristic of lenses that incorporate diffractive/refractive zones in this manner is that the amount of light in the near and distant foci be substantially constant for all pupil sizes. However, it might be desired in certain instances to increase the amount of light in the distant focus as the pupil size increases, for instance under intermediate or low light conditions. One way to increase the amount of light dedicated to distance vision is to restrict the zone producing the second focal point to the central portion of the lens, and to make the outer region of the lens refractive only.

A particular disadvantage associated with the radially symmetric-type of bifocal IOL is the aforementioned problem of halos. In the case of halos, light from the unused foci creates an out-of-focus image that is superimposed on the used foci, in part due to the abrupt change in optical power between adjacent ones of the annular zones. For example, if light from a distant point source is imaged onto the retina of the eye by the distant focus produced by a concentric bifocal IOL, the near focus produced by that IOL may simultaneously superimpose a defocused image on top of the image formed by the distant focus, thus creating a halo effect. Thus, it is not possible to have high contrast images either at the far focus or near focus. Although non-radially symmetric IOLs may partially address halos, such halos are constrained to the part of the field of view where the added power is addressed. In addition, the abrupt optical power changes between zones preclude complete elimination of halos and glare.

Therefore, the need exists for a lens, and a system and method of providing a lens having an optical add power progression that allows for the following: far, near and intermediate vision with good visual performance at all distances; significantly reduced halos and glare; improved contrast sensitivity; and minimized pupil dependence.

SUMMARY OF THE INVENTION

The aspects of the apparatus, system and method of the present invention include an ophthalmic lens having an optic with an anterior surface, a posterior surface, and an optical axis. The ophthalmic lens further includes a first region having a first optical power and a second region having a second optical power. The ophthalmic lens further includes a third region having optical powers that progress from the first optical power to the second optical power. The progression may be uniform or non-uniform. Each of the first and second zones may include a base power and an optical add power. Each of the first, second and progression regions may provide a first focus, a second focus and a plurality of third foci, covering far, near and intermediate distances, respectively.

More particularly, an ophthalmic lens in accordance with the present invention may include an optic comprising a first region having a base optical power and a first optical add power for providing a first focus, a second region having the base optical power and a second optical add power different from the first optical add power for providing a second focus and a third region having the base optical power and a third optical add power comprising a progression of optical add power from the first optical add power to the second optical add power.

In an exemplary embodiment where the power progression is applied vertically, the first region may comprise an uppermost portion of the optic, and may provide a distance vision focus. The uppermost portion may comprise at least the uppermost about 37.5% to 50% of the optic along a vertical diameter of the optic. The second region may comprise a lowermost portion of the optic, and may provide a near vision focus. The lowermost portion may comprise at least the lowermost about 25% of the optic along the vertical diameter of the optic. The third region may comprise a central portion of the optic occupying at least the central-most about 25% of the optic along a vertical diameter of said optic.

The regional divisions of the lens may be chosen to either decrease pupil dependence or enhance determined viewing distances and allow for a proper far focus determination in the refraction procedure, usually performed at photopic light level conditions. More particularly and by way of non-limiting example, in a central 3 mm diameter area, the uppermost approximately about 25%-50% of the optic along a vertical diameter may be defined to achieve far vision, and the complete progression between the far and near addition may occur in the remaining part of the lens between the near and far vision. Other alternative embodiments are envisioned herein, including variations in regional power distributions and added powers. The regional power distributions may also be considered in the vertical or horizontal direction, or in combinations thereof.

A method of providing a progressive intraocular lens according to the present invention may include assessing at least one biometric of a subject eye, assessing a vision correction and at least a multifocal correction required for the subject eye, and indicating a set of intraocular lenses with each lens in the set having at least one optical add power region with the same base power for remedying the vision correction, and different optical add power progressions therebetween for providing the multifocal correction, wherein the at least one biometric indicates at least one in situ aspect of the intraocular lens. The method may further include simulating the optical quality of the patient's eye once implanted with each intraocular lens from that set and selecting the intraocular lens with the corresponding power progression that maximizes patient eye's optical quality.

The method of providing a progressive intraocular lens according to the present invention may be customized. For example, far vision may be achieved by a base power calculated considering the biometric eye data, the near addition may be customized considering typical visual tasks carried out by the patient, and the intermediate addition may be a personalized progression.

A lens system for providing multifocal vision correction, according to the present invention, may include a first focal region, a second focal region and a third region, physically distinct from at least the first focal region and the second focal region. The third region may provide a plurality of third foci representing a progression of optical add power between a first optical add power of the first focal region and a second optical add power of the second focal region. All regions may be joined in a continuous through focus curve that allows for simultaneous far, near and intermediate vision, with a similar optical quality.

Thus, the present invention provides a lens, and a system and method of providing a lens, having an optical add power progression that allows for vision across a range of distances with improved contrast sensitivity, while minimizing halos and glare and pupil dependence.

BRIEF DESCRIPTION OF THE FIGURES

Embodiments of the present invention will be understood with reference to the detailed description in conjunction with the accompanying figures, in which like numerals indicate like aspects, and wherein:

FIG. 9 is a list of Zernike coefficients corresponding to the same eye model as in FIG. 8a for 6 mm entrance pupil at 540 nm;

FIG. 12 is a list of Zernike coefficients corresponding to the same eye model as in FIG. 11a for 6 mm entrance pupil at 540 nm;

FIG. 15 is a list of Zernike coefficients corresponding to the same eye model as in FIG. 14a for 6 mm entrance pupil at 540 nm;

FIG. 17 is a table showing the pupil dynamic of the design presented at FIG. 5;

DETAILED DESCRIPTION

It is to be understood that the figures and descriptions of the present invention have been simplified to illustrate elements that are relevant for a clear understanding of the present invention, while eliminating, for the purpose of clarity, many other elements found in typical implantable optic apparatuses, systems and methods. Those of ordinary skill in the art may thus recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The present invention is directed to apparatuses, systems and methods for providing and/or designing a multifocal ophthalmic lens, such as a multifocal intraocular lens (IOL), that provides varied optical power to enhance vision for different focal distances. The terms "power" and "optical power", as used herein, are defined to include the capability of an optical surface to redirect incident light to a focal point. The optical power may result from reflection, refraction, diffraction, or some combination thereof, and is generally expressed in units of Diopters.

Figure 1:
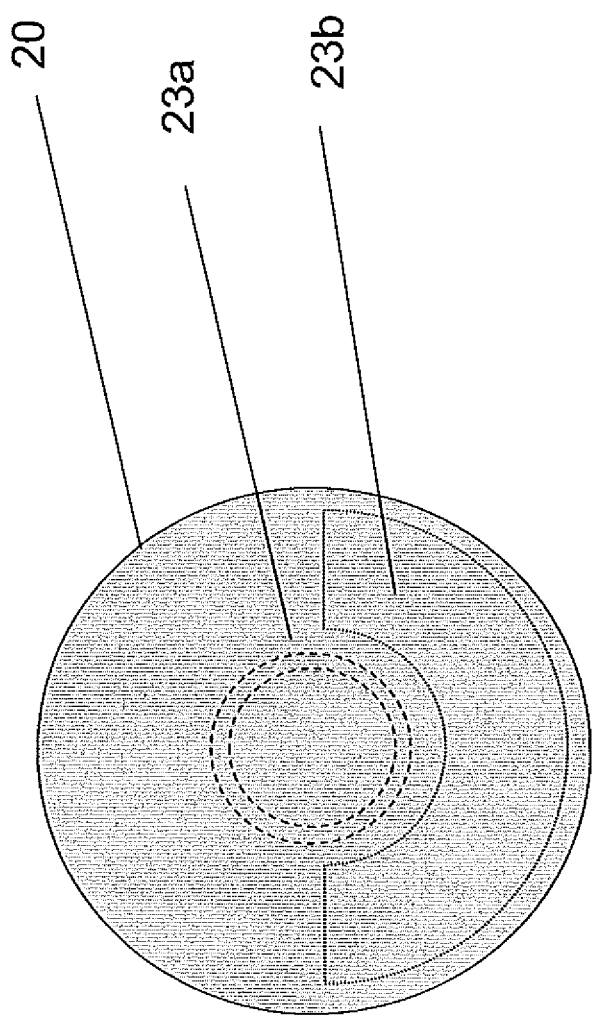
FIG. 1 is a schematic illustration of combinations of prior art bifocal lenses.
Figure 2:
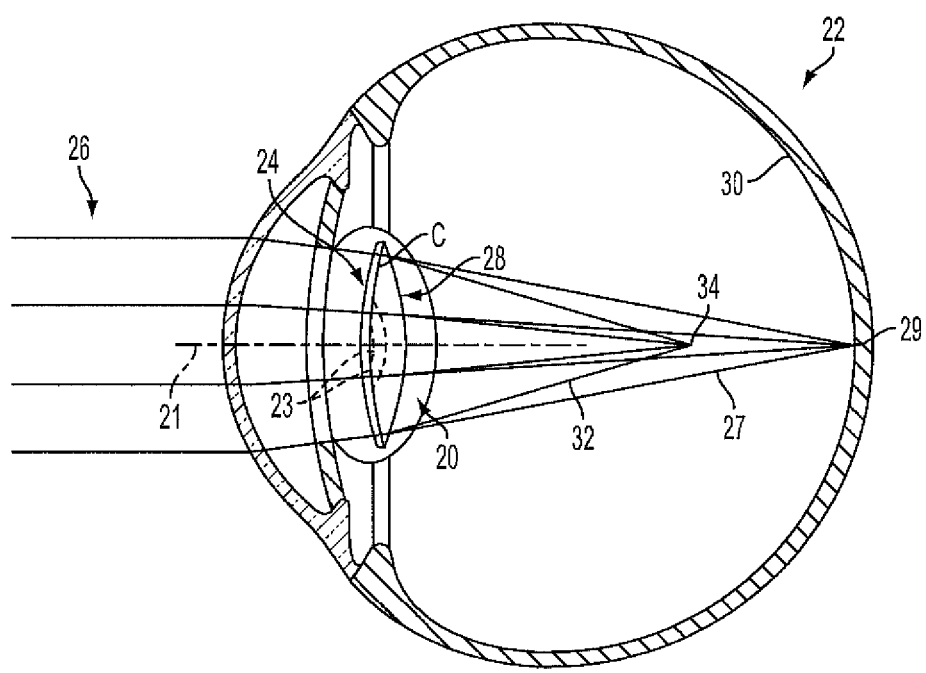
FIG. 2 is a schematic illustration of an eye having implanted therein an intraocular lens viewing an object at infinity.

FIG. 2 illustrates a bifocal IOL 20 with an optical axis 21 disposed in an eye 22. Annular zones 23 for varying optical power are concentrically disposed on an anterior surface 24 having a base curvature, C, and are illuminated by incident light 26 from a distant object that enters the eye 22 in the form of collimated light. Annular zones may be similarly disposed on a posterior surface 28 of lens 20, or on a combination of the anterior and posterior surfaces of lens 20.

A first portion 27 of the incident light 26 may be substantially unaffected by zones 23, or may be affected by some of zones 23, and may be focused to produce a first focus 29 approximately located on a retina 30 of the eye 22. This first focus 29 provides distant vision. A second portion 32 of the incident light 26 may form a second focus 34, located in front of the retina. IOL 20 thus effectively has at least two optical powers due to the combination of the anterior surface 24, the posterior surface 28, and zones 23.

As used herein, the term "near vision' generally corresponds to vision provided when objects are at a distance between about 25 cm to about 50 cm. Conversely, the terms "distance vision" and "distant vision," as used herein, refer to vision wherein objects viewed are relatively far from the subject. The terms "distance vision" and "distant vision" may thus generally correspond to vision provided when objects are at a distance of at least about 2 meters or more away from the subject. The term "intermediate vision" refers herein to the viewing of objects at a distance between near vision and distant vision.

Figure 3:
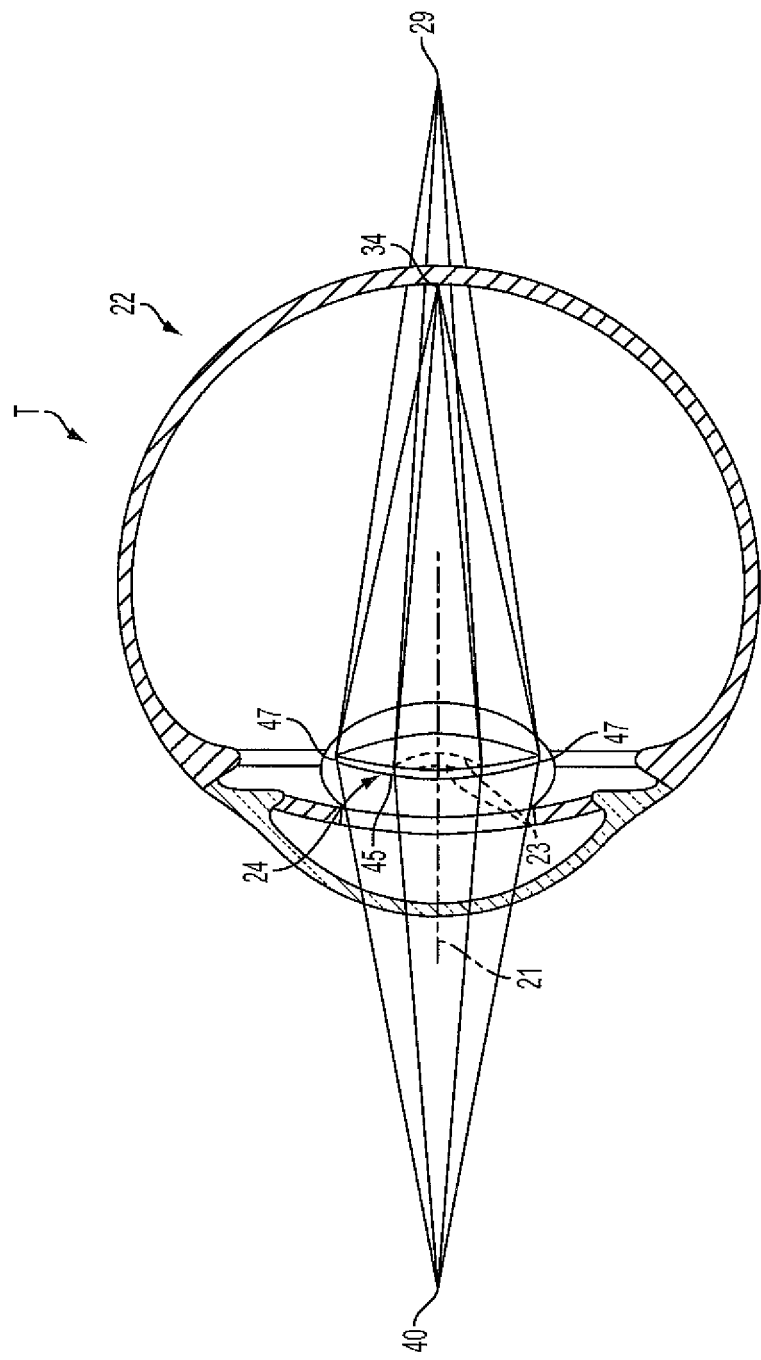
FIG. 3 is a schematic illustration of an eye having implanted therein an intraocular lens viewing an object at a near distance.

FIG. 3 illustrates the performance of IOL 20 for a near object 40 located relatively close to the eye 22. Under these conditions, the distant and near foci 29 and 34, respectively, provided by optic 45 are disposed such that the near focus 34 is approximately located on the retina 30 and the distant focus 29 is approximately located behind the retina 30. Thereby, IOL 20 may function as a bifocal lens that provides a patient with both near and distant vision.

Figure 4:
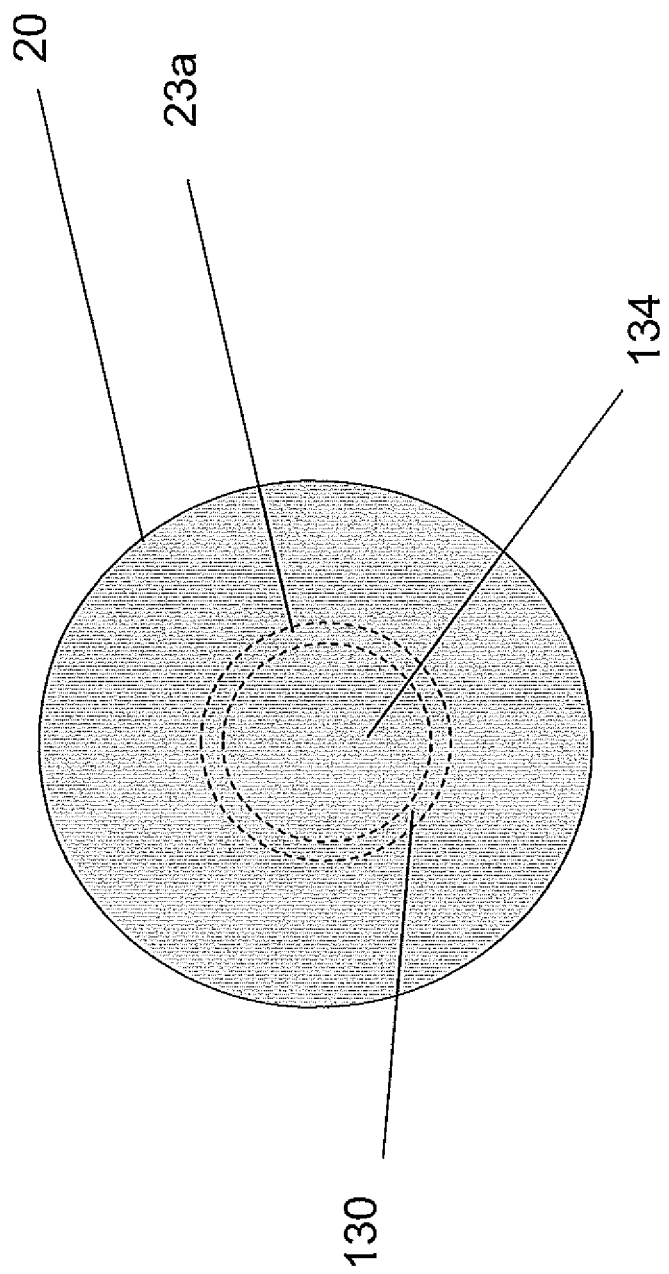
FIG. 4 is a schematic illustration of an intraocular lens having multiple annular zones.

FIG. 4 shows a multifocal lens that provides the optical behavior previously discussed. The plurality of annular zones 23a that provide the bifocal lens functionality may have a particular offset between adjacent zones along the center of the lens. The bifocal characteristics of IOL 20 may be realized, for example, by selecting the offset between adjacent zones to be such that rays to either side of the offset experience a difference in optical path length.

Lens 20 may be an intraocular lens for placement in either the posterior or anterior chamber of a subject eye. As such, lens 20 may be used to replace the natural lens of the eye, such as after removal of the natural lens during cataract surgery. Alternatively, the lens 20 may be a phakic lens disposed in front of the iris, behind the iris, or in the plane defined by the iris. Alternatively, lens 20 may be a corneal implant. Alternatively, lens 20 may be a contact lens or the like used to provide or improve vision.

Lens 20 may be constructed of any commonly employed material or materials used for optics, such as polymethylmethacrylate (PMMA), silicone polymeric materials, acrylic polymeric materials, hydrogel-forming polymeric materials, such as polyhydroxyethylmethacrylate, polyphosphazenes, polyurethanes, mixtures thereof, and the like. The construction material preferably is capable of providing the requisite vision or vision correction, and exhibits biocompatibility with the eye. Lens 20 may be made of or contain photosensitive materials (e.g., photopolymer or silver halide) or a variable refractive index material.

Foldable/deformable materials are particularly advantageous for use in or as lens 20 and/or optic 45, since such deformable materials may be rolled, folded or otherwise deformed and inserted into the eye through a small incision. The lens material preferably has a refractive index allowing a relatively thin, and preferably flexible, optic 45, for example, having a thickness in the range of about 100 microns to about 1000 microns, and preferably about 150 microns to about 500 microns. In embodiments wherein lens 20 is an intraocular lens, optic 45 may have a diameter of about 2 mm or less to about 7 mm or more, and preferably of about 4.0 mm to about 6.0 mm or about 6.5 mm.

In an exemplary embodiment, lens 20 may comprise one or more fixation and/or support members, or "haptics." Haptics 47 may be made of the same material as optic 45 and/or may be integrally formed with optic 45. Alternatively, one or more haptics 47 may be formed separately and attached to optic 45. Haptics 47 may comprise any of a variety of materials that exhibit sufficient supporting strength and resilience, and/or that are substantially biologically inert in the intended in vivo or in-eye environment. Suitable materials for this purpose include, for example, polymeric materials such as silicone polymeric materials, acrylic polymeric materials, hydrogel-forming polymeric materials, such as polyhydroxyethylmethacrylate, polyphosphazenes, polyurethanes, mixtures thereof, and the like.

As illustrated in FIG. 4, annular zones 23a typically include a central zone 134 that is at least partially annular and that is surrounded by another zone or zones 130 that typically have an at least partially annular shape. Whether the add power is achieved via refraction or diffraction, determination of the diameter and height of each of the annular zones 130, 134 is well known in the art and is generally a function of a design wavelength and the desired focal lengths of lens 20. In prior art embodiments of FIG. 4 which reflects refractive technology, each annular zone is provided with a particular optical power, and, to the extent a different focal length is to be provided by others of the annular zone(s) from the first annular zone, those others of the annular zone(s) may be suitably provided with a different optical power than the optical power of the first annular zone.

The annular zones 130, 134 are preferably concentrically offset in the IOL plane so as to form optical add power steps between adjacent zones 130, 134, the steps being selected to produce a predefined relationship between each of the annular zones 130, 134. In certain embodiments, the zones 130 are formed by refractive index variations between the central zone 134 and the other zones 134. Preferably in the embodiment of FIG. 4, the variation in refractive index across the surfaces is in a radial direction from the center of the optic.

However, the abrupt changes in the optical add power steps between different zones 130, 134 of the lens 20 typically generate glare and/or halos, with loss in contrast sensitivity. This is amplified when diffraction is used to generate an extra foci due to the amount of light that is lost in diffraction orders other than those used to achieve multifocality. In addition, intermediate vision is not adequately provided by these types of designs, in part because the design is for enhancing only near and far vision.

Figure 5:
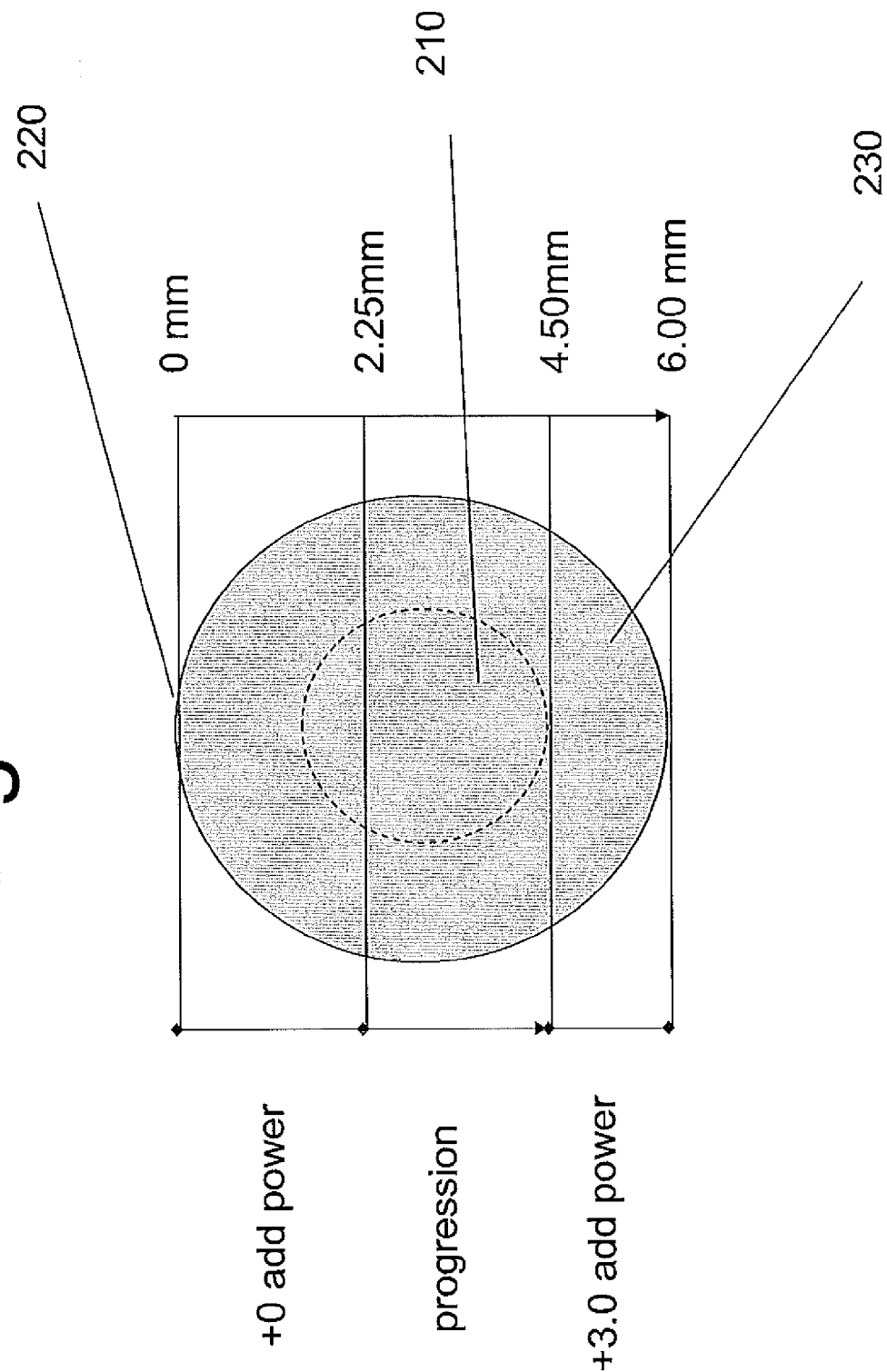
FIG. 5 is a schematic illustration of a multifocal intraocular lens having a vertical optical power progression.

To remedy these disadvantages of the prior art, the present invention provides a design with at least three different zones that provide multifocal vision. An exemplary embodiment is presented in FIG. 5, which shows a lens 20 having three distinct zones 210, 220, 230 that provide multifocal vision. Of note, the dotted line on the lens of FIG. 5 illustrates a central zone (which is 3 mm in diameter in the illustrated exemplary embodiment), rather than illustrating a physical geometric surface feature of lens 20 or a uniform region for optical power. Of further note, zones 210, 220 and 230 may be concentrically or non-concentrically annular, or, as discussed further hereinbelow, horizontal, vertical, oblique or curved. The extension of the different zones can be modified such that any zone may be eliminated or provided with a zero add power in order to enhance the visual acuity at varying distances as required for the patient.

Zones 220, 210, 230 are distinct from zones 130, 134, at least in that there is no abrupt change in optical power as between illustrated central zone 210 and zones 220, 230. More particularly, the optical add power progressively varies across at least a portion of lens 20, and such progression may occur concentrically outward from the center point of central zone 210, vertically from a top portion to a bottom portion of the optic of lens 20 as that lens resides in situ, horizontally from a right to left portion of the optic of lens 20 as that lens resides in situ, and/or in any combinations thereof.

By way of example, when the design is applied vertically, lens 20 may have an optic with a particular diameter, such as 6 mm. From the top of the optic as the optic is positioned in situ, at 37.5% from the topmost point along the vertical diameter, or 2.25 mm along the vertical diameter from the top of a 6 mm diameter exemplary optic, 0 Diopters of optical add power may be provided for all horizontal cross sections across optic 45. For the next 2.25 mm along the vertical diameter of an exemplary 6 mm diameter optic, the optical add power may vertically progress from 0 Diopters to, for example, about +3 Diopters. Along the lowermost portion of optic, such as the lowermost 25% along the vertical diameter (i.e., the lowermost 1.5 mm of the vertical diameter of an exemplary 6 mm diameter optic 45), the optical add power may remain constant, such as at +3 Diopters, for example, or alternatively may follow a secondary progression. The vertical progression(s) may progress at a substantially uniform, constant rate, or may progress at varying rates.

The zone 210 is designed to be non concentric with respect the optic. Considering the 3 mm inner part of the optic, the 25% is included in the zone 220 while the remaining 75% is inside of the zone 210.

For the sake of clarity, as used herein the optical add power is the additional optical power provided in conjunction with a base power for the optic. Of course, those skilled in the art will appreciate, in light of the discussion herein, that the base power of the optic may be calculated in order to achieve emmetropia for far distances.

For a determined regional power distribution, the method by which the power progresses can be defined as follows. In an embodiment, assuming a constant progression of power between the designed for boundaries of optical add power, the horizontal cross-sectional add power in this illustrative 6 mm diameter optic embodiment may follow the equation:

| | |
|---|---|
| 0 D | $0 < y' < 2.25$ mm |
| $1.33*(y' - 2.25)$ D | $2.25 < y' < 4.5$ mm |
| 3 D | $y' > 4.5$ mm | where y' is the distance from reference 0 mm at the top of the vertical diameter of the optic. Thus, the add power along a horizontal cross section through the center point of optic (i.e., where y'=3) is, in this exemplary embodiment:

$1.33*(3-2.25)=1.00$ D. In alternative embodiments, y' may be measured from other points at the edge of the optic, e.g. at the far right point of the horizontal diameter of the optic.

The same horizontal cross sectional add power may be expressed by measuring the vertical distance from the center of the lens:

| | |
|---|---|
| 0 D | $-3 < y < -0.75$ mm |
| $1.33*(y + 0.75)$ D | $-0.75 < y < 1.5$ mm |
| 3 D | $y > 1.5$ mm | where y represents the vertical distance with respect to the center of the lens. Such a power distribution is identical to that previously presented.

In another embodiment with the same regional power distribution, the method of designing the progression might be imposed by a step function. In that case, the power may be as follows:

| | |
|---|---|
| +0D | $0 < y' < 2.25$ mm |
| +1D | $2.25 < y' < 3.375$ mm |
| +2 D | $3.375 < y' < 4.5$ mm |
| +3 D | $4.5 < y' < 6$ mm | when the vertical distance (y') is measured from the uppermost part of the lens or:

| | |
|---|---|
| +0 D | $-3 < y < -0.75$ mm |
| +1D | $-0.75 < y < 0.375$ mm |
| +2 D | $0.375 < y < 1.5$ mm |
| +3 D | $1.5 < y < 3$ mm | when y represents the vertical distance to the center of the lens.

Figure 6:
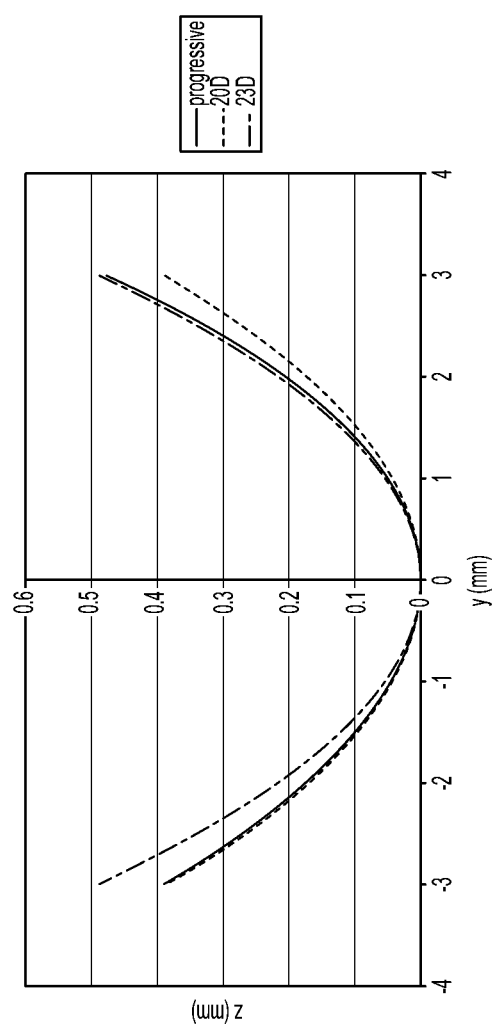
FIG. 6 is the sag representation of an embodiment in comparison with two lenses with a fixed power.

FIG. 6 shows the sag corresponding to two aspheric lenses with different power (ie. 20D and 23D). The sag of the progressive design corresponding to the previous embodiment when the base power is 20D is also represented in that plot. In this context, base power is the power providing far vision. Thus, in this particular example, the progressive lens is composed by the curvatures of 20D, 21D, 22D and 23D, according the previous power profile. FIG. 6 shows how the sag progressively changes from that corresponding to a 20D, in the uppermost part of the lens, to that related to a 23D, in the lowermost part of the lens. Therefore, the addition of +3D is achieved, by following the progression described in the previous embodiment.

The tangential sag defined in such a way may be then fitted according to (eq 1):

$$z(y) = \frac{cy^2}{1+\sqrt{1-(k+1)y^2 c^2}} + k1y + k3y^3 + k4y^4 + k5y^5 + +k6y^6 + k7y^7 + k8y^8$$

Therefore, the vertical meridian of the lens is defined according to an extended aspheric shape, with a curvature c and a conic constant k, although other symmetrical or non symmetrical terms (k1 until k8) are considered in order to achieve the fitting of the corresponding surface. The exemplary embodiment showed in FIG. 6, may be fitted according the previous formula selecting the curvature and conic constant corresponding to the base power (20D in the exemplary embodiment). The results of that fitting define the tangential sag of the lens. To further define the complete design, an extended biconic surface is used (eq. 2):

$$z(x,y) = \frac{cy^2 + cx^2}{1+\sqrt{(1-(k+1)y^2 c^2 - (k+1)x^2 c^2)}} + k1y + k3y^3 + k4y^4 + k5y^5 + +k6y^6 + k7y^7 + k8y^8$$

Figure 7:
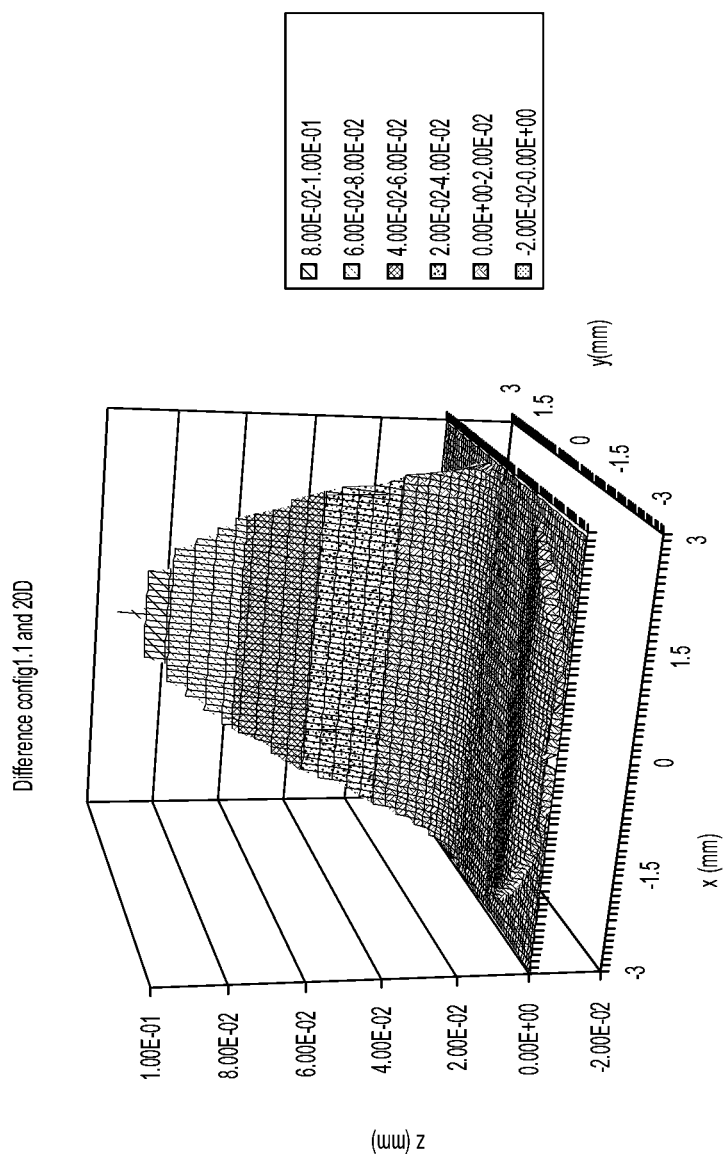
FIG. 7 is the difference between the lens surface result of a preferred embodiment and the surface of a 20D lens.

Thus, the curvature and conic constant used for fitting the tangential sag are also considered in generating the corresponding meridional sag, which is defined as a standard aspheric surface, defining the combination of the complete surface of the lens. FIG. 7 presents the difference in shape between the exemplary design and the base power lens (ie. 20D). This difference is zero in the uppermost part of the lens, while the difference increase with the vertical distance. Therefore, the method herein described provides a lens design that corresponds to FIG. 5, when a step power progression is imposed.

The optical behavior of such a design can be computationally tested. Those skilled in the art will appreciate that, for example, an optical design software simulation may be employed in order to provide such modeling, for example, using Zemax® software by Zemax Development Corporation of Bellevue, Wash. A computational model of an average eye may be used in order to evaluate the performance of the design. This computational model may comprise the most representative optical structures of the eye, such as the cornea, the pupil and the retina. Average corneal aberrations may also be considered in order to further mimic the average eye. An IOL with a determined design may be inserted in such a model and different optical quality parameters may be calculated. Those calculations may be performed in white light conditions to closely represent the real behavior of the design, once implanted into the eye.

Figure 8A:
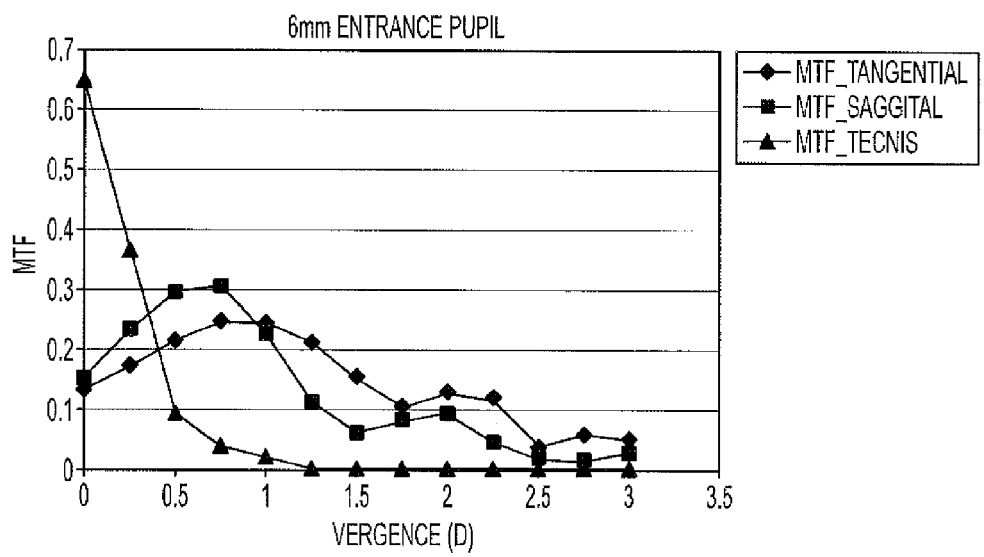
FIGS. 8a and 8b are the simulated through focus MTF in the tangential and sagital direction for the design corresponding to FIG. 7 for different entrance pupils once implanted in an average eye model in comparison to that provided by a marketed lens.
Figure 8B:
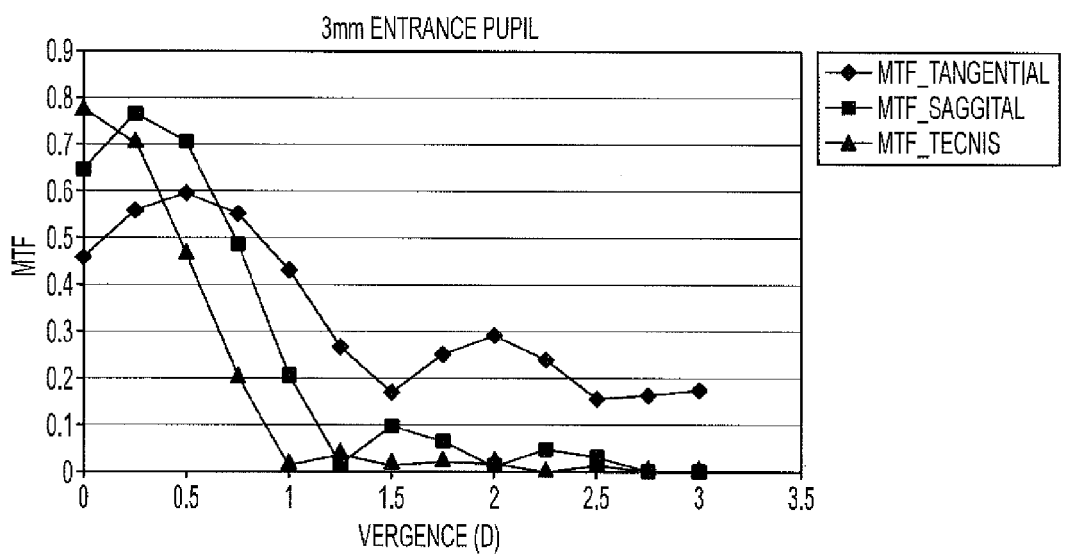

FIGS. 8a and 8b illustrate the tangential and sagittal modulation transfer function (MTF) at 30 cycles per millimeter calculated for different vergences in such a model eye with the exemplary design described above for two different entrance pupils. For comparison purposes, the through focus MTF of a monofocal lens is also shown.

The optical quality of the eye containing the progressive design may also be assessed by the eye's model wavefront aberrations. FIG. 9 lists the Zernike terms until $6^{th}$ order calculated at 6mm entrance pupil for 540 nm. It is understood that the design generates some amount of non symmetrical aberrations, such as astigmatism, coma and trefoil.

The design represented at FIG. 5, with the vertical regional power distribution described before and comprising a step power progression may have variants. In another embodiment, the same sag (i.e. the same optical power progression) as presented in FIG. 6 may also be fitted to eq 1 according to a different power. Thus, the curvature and conic constant may be different to that defining the lens' base power. In that case, the curvature and conic constant considered to fit the vertical power progression may also be used in the x direction in order to generate the extended biconic surface which defines the design, according eq 2.

Thus, in an alternative exemplary embodiment, the sag at FIG. 6, that has 20D as base power, may be fitted using the curvature and conic constant for a 21D lens, according to eq. 1. The corresponding lens surface is generated therefore using an extended biconic surface that in the x direction is defined by the radius and conic constants corresponding to 21D and according to the achieved fitting in the y direction, as stated in eq. 2.

Figure 10A:
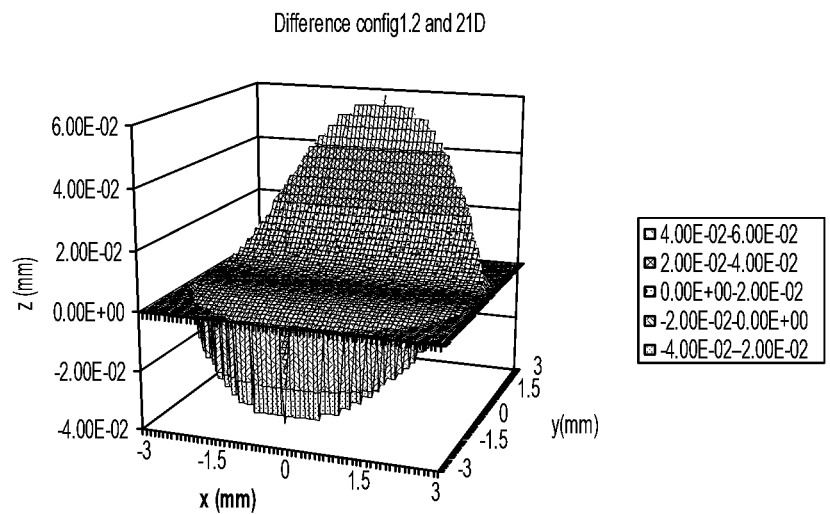
FIGS. 10a and 10b is the difference between the lens surface result of an alternative embodiment and the surface of a 21D lens and 20D respectively.
Figure 10B:
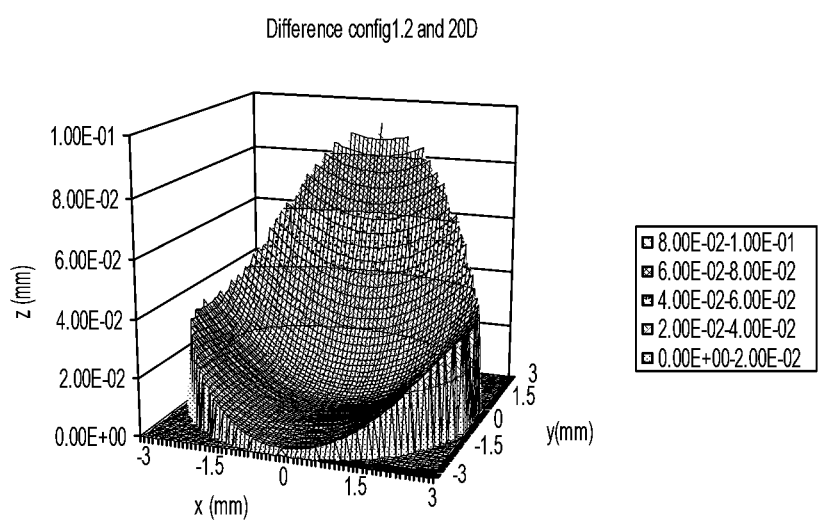
Figure 11A:
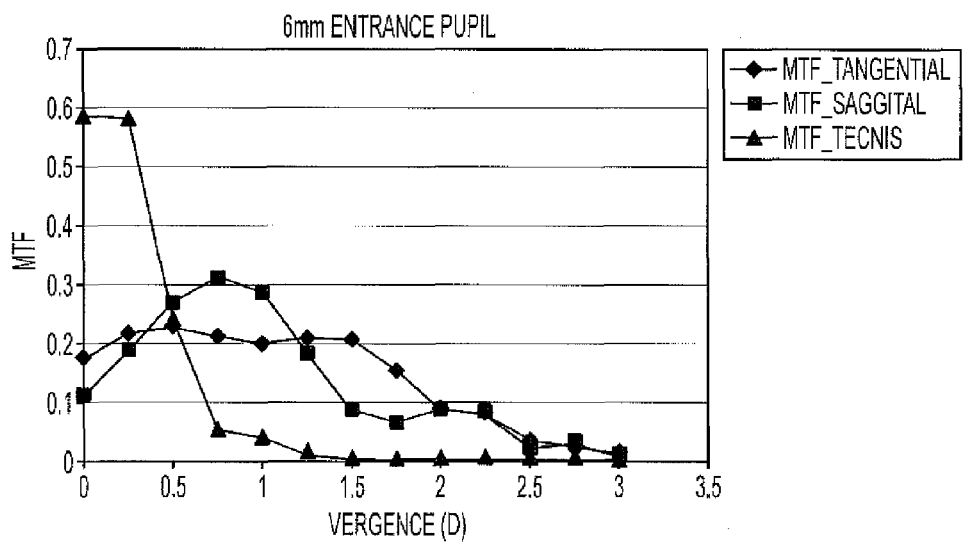
FIGS. 11a and 11b are the simulated through focus MTF in the tangential and sagital direction for the design corresponding to FIG. 10 for different entrance pupils once implanted in an average eye model in comparison to that provided by a marketed lens.
Figure 11B:
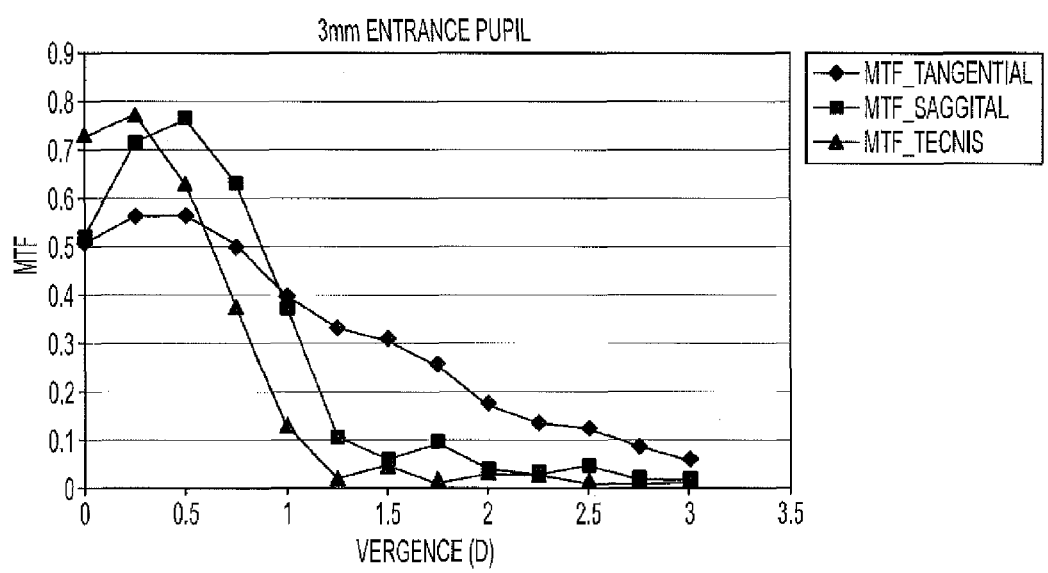

FIG. 10a shows the difference between such a design and the surface defining the curvature and conic constant, which is that corresponding to a 21D lens. FIG. 10b shows the difference between that exemplary design and the surface of a 20D lens, that is the base power lens. FIGS. 11a and 11b show the tangential and sagittal through focus MTF calculated in the same eye model as previously described when this exemplary design is inserted. FIG. 12 presents the wavefront aberrations of the eye at 6 mm entrance pupil for 540 nm. Those skilled in the art may appreciate that this alternative embodiment introduces some amount of non symmetrical aberrations, although the amount of induced astigmatism is lower than in the previous exemplary embodiment, presented at FIG. 9. Therefore, the present embodiment of the invention is a power progression lens with reduced astigmatism induction.

In another alternative embodiment, the curvature and conic constant corresponding to the x direction may be different to that defining the tangential progression. Thus, the surface is represented by eq. 3:

$$z(x,y) = \frac{c_y y^2 + c_x x^2}{1+\sqrt{(1-(k_y+1)y^2 c_y^2 - (k_x+1)x^2 c_x^2)}} + k1y + k3y^3 + k4y^4 + k5y^5 + +k6y^6 + k7y^7 + k8y^8$$

where the cx and kx and cy and ky are the curvature and conic constant respectively in the x and y direction.

The power progression concept herein described may be applied in orientations other than vertically. In an alternative embodiment, the results from the fitting corresponding to the sag of the power progression may also be used to generate an additional progression in the x direction, according to eq 4:

$$z(x,y) = \frac{c_y y^2 + c_x x^2}{1+\sqrt{(1-(k_y+1)y^2 c_y^2 - (k_x+1)x^2 c_x^2)}} + k1_y y + k3_y y^3 + k4_y y^4 + k5_y y^5 + +k6_y y^6 + k7_y y^7 + k8_y y^8 + k1_x x + k3_x x^3 + k4_x x^4 + k5_x x^5 + +k6_x x^6 + k7_x x^7 + k8_x x^8$$

where the kix and kiy with i=1,8 are the results from the fitting representing the power progression in the x and y direction respectively with respect to the curvatures and conic constants cx and kx, and cy and ky respectively. Those skilled in the art may understand that the power progression applied in the x and y direction may be the same, fitted or not against the same base power, or may be different.

Figure 13:
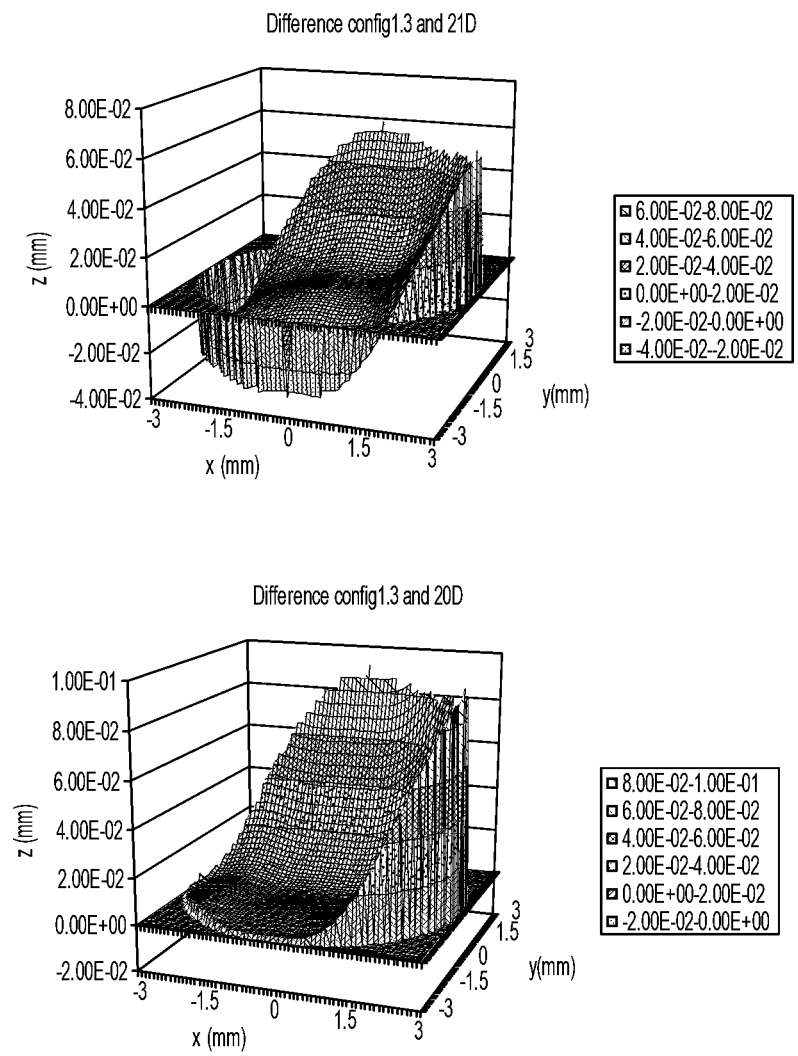
FIG. 13 is the difference between the lens surface result of another alternative embodiment and the surface of a 21D lens and 20D respectively.
Figure 14A:
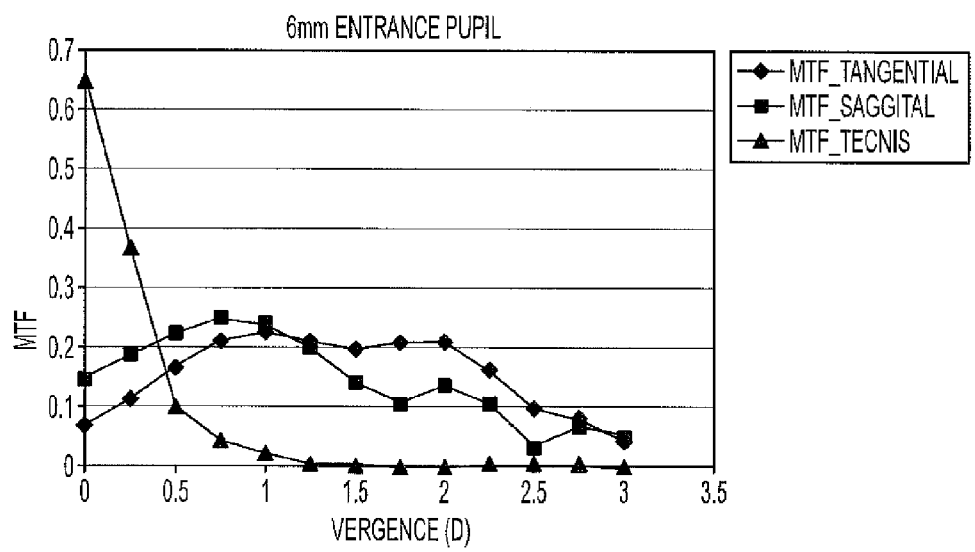
FIGS. 14a and 14b are the simulated through focus MTF in the tangential and sagital direction for the design corresponding to FIG. 13 for different entrance pupils once implanted in an average eye model in comparison to that provided by a marketed lens.
Figure 14B:
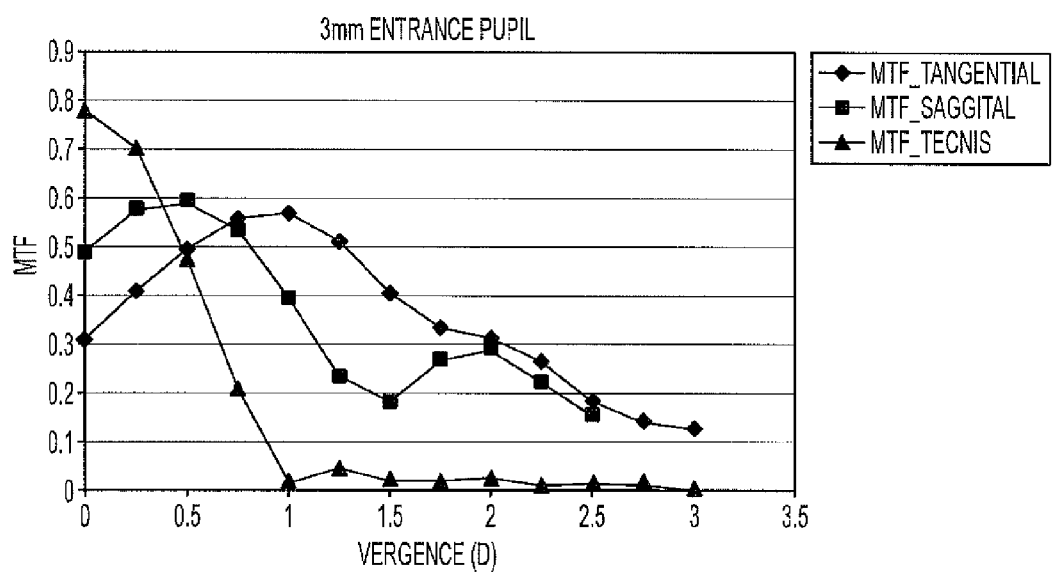

In an exemplary embodiment, the progressive surface is generated by applying the power progression corresponding to FIG. 6 fitted against the 20D in the x direction. In the y direction the same power progression is applied but fitted against 21D. Thus, this is a double progression (ie. in the x and y direction), defined according eq 4, with two different curvatures and conic constants respectively in x and y. FIG. 13 shows the difference between this surface and a 20D and 21D respectively. Such a surface represents a curved power progression. FIGS. 14a and 14b represent the optical quality of the model eye previously described once implanted with the lens herein described. FIG. 15 lists the Zernike coefficients of the eye model once implanted with the herein showed design.

The step progression which defines the sag at FIG. 6 may be represented by more steps with, alternatively, different powers. The method describing the tangential fitting and the biconic surface generation may also be applied to that alternative power progression.

The minimum or maximum add power of the exemplary embodiment are merely illustrative. More particularly, the minimum add power may be greater than 0 Diopters, and/or the maximum add power may be less than or greater than +3 Diopters. For example, the minimum or maximum add power may be modified to provide a customized performance for near, intermediate or distance vision of the subject.

Likewise, the point along the diameter at which the progression begins or ends may be modified, such as in order to customize performance of the optic. Moreover, multiple progressions may occur along the diameter, such as wherein a progression is implemented from 0 mm to 2.25 mm in the exemplary 6 mm diameter optic, the same or a different progression is implemented from 2.25 mm to 4.5 mm, and the same, or yet a different, progression is implemented from 4.5 mm to 6 mm. Similarly, one or all progressions may be uniform progressions, or may be non-uniform progressions, in order to customize the vision outcome by subject. The power addition progression may be displaced with respect the center of the optic.

Figure 16:
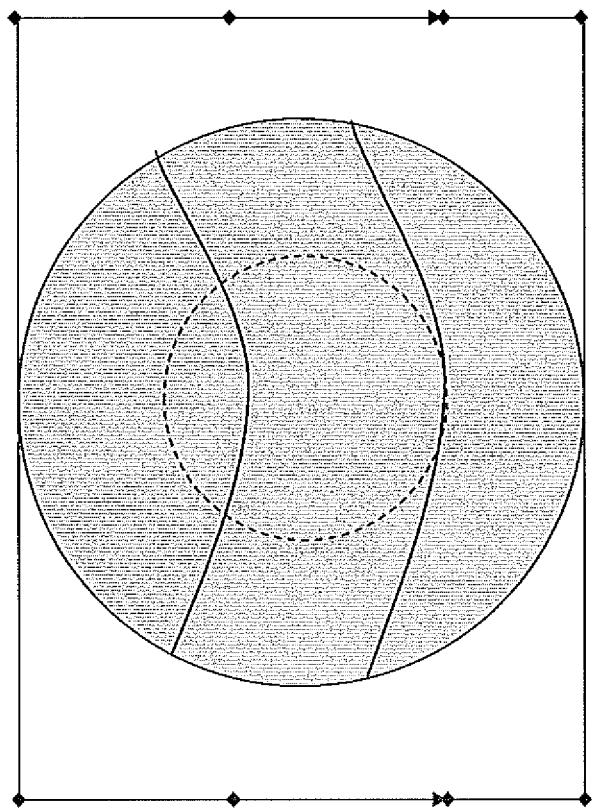
FIG. 16 is a schematic illustration of a multifocal intraocular lens having a curved optical power progression.

With reference to FIG. 5, an exemplary embodiment is discussed in which add power is constant along each horizontal cross section. Those skilled in the art will appreciate that the add power may be constant along a curve, rather than along a horizontal cross section, as illustrated in FIG. 16. Similarly, zones 210, 220, 230 may be provided concentrically and, in such a case, add power may be constant along a curve, and/or may be non-constant along a horizontal cross section of optic 23c, as occurs in the design corresponding to FIG. 13.

In the present example, the power addition progression is displaced with respect the center of the optic. By this way, pupil independence is addressed. It is important to note that the far focus should be clearly appreciable by the patient in order to avoid near dependent designs that could lead to confusion for the subject in the far focus finding during the refraction process, thus eliminating the multifocal effect of the optic.

FIG. 17 illustrates the behavior of the optic presented at FIG. 5 with respect to the physical pupil size. As shown, for a 3 mm pupil, far and intermediate viewing distances may be enhanced. As the pupil size increases to 4 mm, both the near and far viewing distances are enhanced to the same or substantially same ratio, thus indicating that the design of the present invention may be pupil independent. Further, for larger pupils, near focus may be particularly enhanced with respect to far and/or intermediate focus.

It will be appreciated that confining the add power progression to the central zone, in accordance with the present invention, may avoid significant pupil dependence. Further, the add power progression may avoid abrupt power changes that can lead to halos, glare and decreased contrast sensitivity, while being particularly beneficial for intermediate vision.

Although an optical add power progression in accordance with the present invention may cause astigmatism, coma, and/or other aberrations, a customized simulation executed prior to implantation may allow for anticipation of such aberrations, and may indicate one or more design selections, as discussed herein, in order to maximize the optical performance of the coupling between the design and those aberrations added by the patient.

Figure 18:
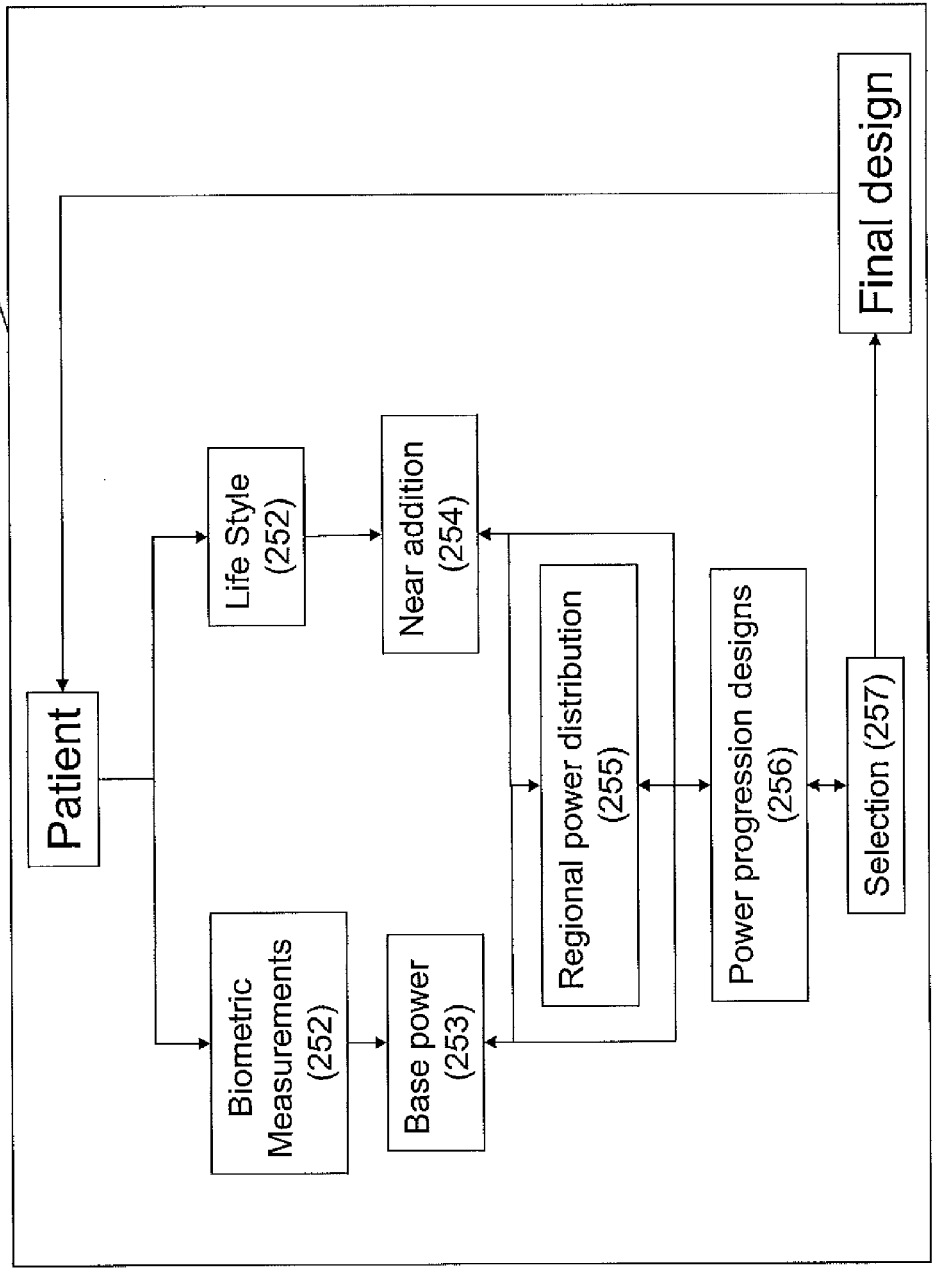
FIG. 18 is a flow diagram illustrating a method of providing an intraocular lens.

FIG. 18 illustrates a method 250 of implementing the invention discussed hereinthroughout. The method 250 may include the steps of assessing the biometric measurements of the eye at step 252, such as to define a base power to achieve emmetropia at far distance at step 253. Further, step 252 may include questions related to the patient's life style (common habits, work, etc.), such as to define an optimal near power addition at step 254. The output of steps 252, 253 and 254 may, in combination, allow for a determination of the regional power distribution at step 255. Step 256 may additionally include further designs, such as for particular enhancement of far, near and/or intermediate vision, as herein described. At step 257, simulations may be used to indicate any aberrations resulting from the add power progressions at steps 256 and its impact when introduced into the patient's eye, and at step 257 a selection between all possible designs is made according to prior simulations, leading to the final customized lens design. Those skilled in the art will appreciate that certain of the steps of method 250 may be performed using computing and/or simulations.

Figure 19:
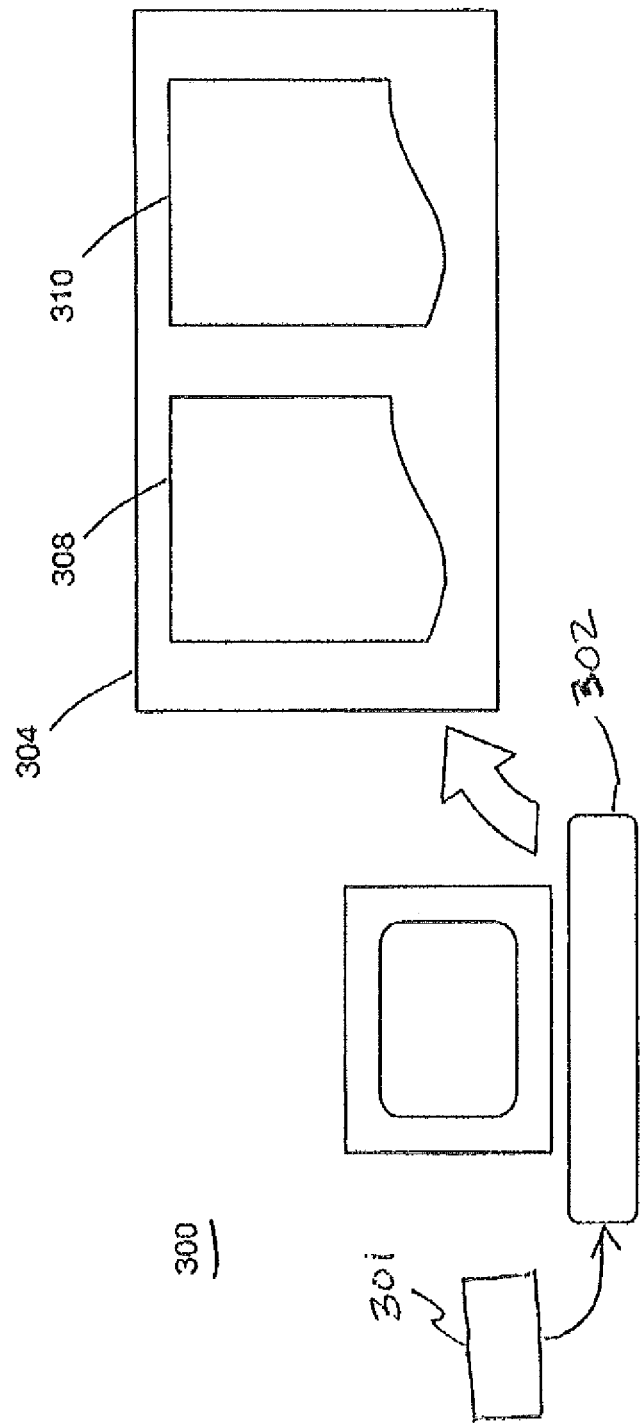
FIG. 19 is a graphical representation of the elements of computing system for selecting an intraocular lens.

More particularly, and as illustrated in FIG. 19, the present invention may be implemented in a clinical system 300 that is capable of assessing the eye's biometric measurements and of performing the calculations set forth in method 250. The system 300 may include a biometric reader 301 that may take or formulate measurements needed for at least a base power calculation 301, a processor 302, and a computer readable memory 304 coupled to the processor 302. The computer readable memory 304 includes therein an array of ordered values 308 and sequences of instructions 310 which, when executed by the processor 302, cause the processor 302 to design an IOL and power progression of the IOL configured for implantation into the eye of the subject presenting the biometric readings to biometric reader 301. The array of ordered values 308 may comprise data used or obtained from method 250 or other methods consistent with embodiments of the invention. The sequence of instructions 310 may include one or more steps of method 250 or other methods consistent with embodiments of the invention.

The processor 302 may be embodied in a general purpose desktop or laptop computer, and/or may comprise hardware associated with biometric reader 301 specifically for selecting an IOL having an add power progression for placement into the eye of the subject. In certain embodiments, the system 300 may be configured to be electronically coupled to another device, such as one or more instruments for obtaining measurements of an eye or a plurality of eyes. Alternatively, the system 300 may be embodied in a handheld device that may be adapted to be electronically and/or wirelessly coupled to one or more other devices.

Those of ordinary skill in the art may recognize that many modifications and variations of the present invention may be implemented without departing from the spirit or scope of the invention. Thus, it is intended that the present invention covers such modifications and variations of this invention provided they come within the scope of the discussion herein and any appended claims, and any equivalents thereto.

The invention claimed is:

1. An ophthalmic lens, comprising:
an optic having a vertical diameter and a horizontal diameter, comprising:
a first region having a first optical power for providing a first focus, wherein the first region comprises an uppermost portion of said optic and wherein the first optical power is constant along each horizontal cross section in the first region;
a second region having a second optical add power different from the first optical power for providing a second focus, wherein the second region comprises a lowermost portion of said optic and wherein the second optical add power is constant along each horizontal cross section in the second region; and
a third region having at least the first optical power and a plurality of third optical add powers comprising a progression of optical add powers increasing along the vertical diameter from the first optical power to the second optical add power, wherein the third region comprises a central portion of said optic, wherein an uppermost boundary of the third region is above a center of said optic and a lowermost boundary of the third region is below the center of said optic, and wherein each of the plurality of third optical add powers is constant along a horizontal cross-section in the third region parallel to the horizontal diameter.

2. The lens of claim 1, wherein the uppermost portion comprises at least the uppermost 25% along the vertical diameter of said optic.

3. The lens of claim 1, wherein the uppermost portion comprises the uppermost 37.5% along the vertical diameter of said optic in the complete optic.

4. The lens of claim 1, wherein the second focus comprises a near vision focus.

5. The lens of claim 1, wherein the lowermost portion comprises at least the lowermost 25% along the vertical diameter of said optic.

6. The lens of claim 1, wherein the central portion comprises a centralmost of at least 25% along the vertical diameter of said optic.

7. The lens of claim 1, wherein the central portion comprises a centralmost of at least 37.5% along the vertical diameter of said optic.

8. The lens of claim 1, further comprising at least one haptic that at least partially supports said optic within a subject eye.

9. The lens of claim 1, wherein the progression of optical add powers in the third region is continuous.

10. The lens of claim 1, wherein the progression of optical add powers in the third region is step-wise.

11. The lens of claim 1, wherein the progression of optical add powers in the third region is uniform.

12. The lens of claim 1, wherein the progression of optical add powers in the third region is non-uniform.

13. The lens of claim 1, wherein the third region has a constant height measured along a vertical diameter of the optic.

14. The lens of claim 1, wherein the third region is asymmetric with respect to the center of the optic.

* * * * *